(12) United States Patent
Garcia-Rubio et al.

(10) Patent No.: US 7,691,642 B1
(45) Date of Patent: Apr. 6, 2010

(54) SPECTROPHOTOMETRIC METHOD AND APPARATUS FOR THE CROSS-MATCHING OF PLATELETS

(75) Inventors: Luis Humberto Garcia-Rubio, Temple Terrace, FL (US); Robert Potter, Tampa, FL (US); German Leparc, Tampa, FL (US); Sharyn Orton, Frederick, MD (US); Yvette Mattley, Tampa, FL (US); Christina Bacon, Tampa, FL (US)

(73) Assignee: University of South Florida, Tampa, FL (US)

( * ) Notice: Subject to any disclaimer, the term of this patent is extended or adjusted under 35 U.S.C. 154(b) by 404 days.

(21) Appl. No.: 11/164,466

(22) Filed: Nov. 23, 2005

Related U.S. Application Data

(60) Continuation of application No. 09/861,781, filed on May 21, 2001, now Pat. No. 6,984,526, which is a division of application No. 09/206,630, filed on Dec. 7, 1998, now abandoned, which is a continuation-in-part of application No. 08/775,654, filed on Dec. 31, 1996, now abandoned, which is a continuation-in-part of application No. 08/385,717, filed on Feb. 8, 1995, now Pat. No. 5,589,932.

(51) Int. Cl.
*G01N 33/48* (2006.01)
(52) U.S. Cl. .............................. 436/163; 436/1; 436/2; 436/44; 436/46; 436/50; 436/55; 436/61; 436/164; 436/166; 436/171; 435/2; 435/4; 435/374; 435/284.1; 435/287.1; 422/58

(58) Field of Classification Search .................. 435/1.2, 435/2, 4, 5, 7.2, 29, 374, 284.1, 287.1; 436/517, 436/518, 10, 63, 69, 164, 166, 171, 172, 436/1, 2, 44, 46, 50, 55, 61, 163; 422/55, 422/58
See application file for complete search history.

(56) References Cited

U.S. PATENT DOCUMENTS 4,505,708 A * 3/1985 Gajewski et al. ............ 604/408
5,616,457 A * 4/1997 Garcia-Rubio ................. 435/4

OTHER PUBLICATIONS

Farrugia et al., Platelet size analysis in the quality assurance of platelet concentrates for transfusion, Clinical and Laboratory Haematology 17(1): 51-55 (Mar. 1995) (Abstract).*

(Continued)

*Primary Examiner*—Gailene R Gabel
(74) *Attorney, Agent, or Firm*—Michele L. Lawson; Smith & Hopen, P.A.

(57) ABSTRACT

A method and apparatus for characterizing the type of a blood sample and a variety of blood components are provided wherein a transmission spectrum of the sample is collected over a predetermined wavelength range. For blood typing, this spectrum is then compared with a set of control spectra collected from control blood samples having known blood types, from which the type of the blood sample can be determined. Further methods and apparatus are provided for determining the viability of and for cross matching a platelet unit. Additional method and apparatus permit analysis of the sample for the presence of a contaminant, Particles can also be counted in the sample, even when present in low concentrations, including white blood cell.

8 Claims, 11 Drawing Sheets pH Effects on the Absorbance of Phenol Red

OTHER PUBLICATIONS

Sanchez Gomez et al., Potency assay of diphtheria antitoxin in Vero cell microcultures, Revista LatinoAmericana de Microbiologia 38(2): 97-110 (Apr.-Jun. 1996) (Abstract).*

Booth et al., Bacterial Degradation of Plasticized PVC, J. Appl. Bact. 31: 305-310 (1968).*

* cited by examiner

SPECTROPHOTOMETRIC METHOD AND APPARATUS FOR THE CROSS-MATCHING OF PLATELETS

CROSS-REFERENCE TO RELATED APPLICATION

This application is a continuation of application Ser. No. 09/861,781, filed on May 21, 2001, now U.S. Pat. No. 6,984,526, the contents of which are herein incorporated by reference, which is a division of application Ser. No. 09/206,630, filed Dec. 7, 1998, now abandoned, the contents of which are incorporated herein by reference, which is a continuation-in-part of application Ser. No. 08/775,654, "Spectrophotometric Method and Apparatus for the Cross-Matching of Platelets," filed on Dec. 31, 1996, now abandoned, which is a continuation-in-part of application Ser. No. 08/385,717, "Spectrophotometric Method and Apparatus for the Characterization of Blood and Blood Types," filed on Feb. 8, 1995, now U.S. Pat. No. 5,589,932, issued on Dec. 31, 1996, commonly owned with the present invention.

GOVERNMENT SUPPORT

This invention was made with U.S. Government support under Grant RII-850756 from the National Science Foundation. The Government has certain rights in this invention.

BACKGROUND OF THE INVENTION

1. Field of the Invention

The present invention relates to the characterization of blood types and blood components, and, more particularly, to the spectrophotometric characterization of blood types and blood components.

2. Description of Related Art

Current technology for blood typing or for the diagnosis of pathogens requires analysis by microscopy and/or immunoassay techniques. Specifically, for blood typing, an agglutination reaction is typically used that results from the association of specific antibodies with antigens present on the erythrocyte (red blood cell) surface. The disadvantages of this procedure are that it requires significant amounts of time, trained individuals, and well-equipped laboratory facilities. For blood typing, for instance, an involved laboratory procedure is needed to detect the cell surface antigens. (See, for example, the Technical Manual of the American Association of Blood Banks, Bethesda, Md., 1996.)

In a particular method, an instrument such as that made by Olympus (for example, Model PK-7200, Olympus, Lake Success, N.Y.) is used to detect light obfuscation in agglutinated blood samples to which commercial monoclonal antibodies have been added.

The presence of weak antigens (e.g., weak D) may only be detected by an indirect antiglobulin procedure after incubation of the test red cells with anti-D.

A reliable test for platelet viability does not exist at present. Typically platelet-rich plasma units are discarded after 5 days, and/or pH measurements, which must be performed by invading the storage container, are made (pH decreases with storage time owing to continued metabolism). Visual inspection is also performed, with a "shimmering" indicating the presence of viable, discoid-shaped platelets, although this is obviously not a quantitative measure of viability.

Bacterial contamination is another factor that is of concern in blood product storage, leading to the discarding of units after a predetermined time (e.g., 5 days for platelets). The danger of contamination results from the storage of platelet units at room temperature to maintain viability. Storage at this temperature, however, can lead to bacterial contamination, leading to infection upon infusion into a patient. At present the only reliable method for detection of such contamination is aerobic and anaerobic culturing, with visual detection of bacterial colonies.

Platelet cross-matching is recommended for patients who are refractory to routine platelet transfusions, such as those with hematologic disorders, those with viral infections, or those who have experienced alloimmunization through pregnancy or transfusion. A method known for antibody detection is a solid-phase system (Capture-P, Immucor, Inc., Norcross, Ga.). This system requires a multiplicity of steps, including transferring samples to microtitration wells, centrifugation, washing, agitation, incubation, and further centrifugation.

Cell component counting is another important characterization protocol. White blood cells, for example, can be difficult to count if they are present in small numbers. At present automated hematology analyzers that employ light scattering techniques are used, but these can introduce a high error when determining counts for low sample numbers. In cases of leukoreduced blood products with lower numbers of white blood cells, staining and microscopy or flow cytometry are typically used.

Another limitation of the currently employed technology is a lack of on-line capability for the characterization of blood components, as well as a lack of portable instrumentation capable of detecting, counting, and classifying specific blood components. The problem of portable instrumentation and suitable methods of analysis and diagnosis is particularly relevant to the medical industry, where the need for rapid analysis and diagnosis often involves life-threatening situations. Although the analytical instrumentation used in medical and clinical laboratories has improved considerably over the past decade, there are still no suitable techniques capable of detecting, classifying, and counting on-line critical cell populations and/or pathogens in blood and other bodily fluids. Typically the particles of interest have sizes ranging between 0.5 and 20 µm, and, in many instances, are present in fairly dilute concentrations.

As is known from spectroscopy theory, a measure of the absorption of a solution is the extinction coefficient, which also provides a measure of the turbidity and transmission properties of a sample. Spectra in the visible region of the electromagnetic spectrum reflect the presence of certain metal ions, complexes, and molecules with extensive conjugated aromatic structures. In the near-uv region small conjugated ring systems affect absorption properties. However, suspensions of very large particles are powerful scatterers of radiation, and in the case of microorganisms, the light scattering effect is sufficiently strong to mask or distort absorption effects. It is therefore known to use uv/vis spectroscopy to monitor purity, concentration, and reaction rates of such large particles.

Many attempts have been made to estimate the particle size distribution (PSD) and the chemical composition of suspended particles using optical spectral extinction (transmission) measurements. However, previously used techniques require that either the form of the PSD be known a priori or that the shape of the PSD be assumed. One of the present inventors has applied standard regularization techniques to the solution of the transmission equation and has demonstrated correct PSDs of a large variety of polymer lattices, protein aggregates, silicon dioxide particles, and microorganisms.

It is also possible to use the complementary information available from simultaneous absorption and light scattering measurements at multiple angles for the characterization of the composition and molecular weight of macromolecules (Garcia-Rubio, 1993; and "Multiangle, Multiwavelength Particle Characterization System and Method," U.S. patent application Ser. No. 08/489,940, filed Jun. 13, 1995, now abandoned, and continuation application thereto U.S. patent application Ser. No. 08/780,828, filed Jan. 10, 1997, now U.S. Pat. No. 5,808,738, the disclosures of which are incorporated herein by reference).

SUMMARY OF THE INVENTION

It is therefore an object of the present invention to provide a spectroscopic technique for the characterization and differentiation of blood types.

It is a further object to provide such a technique for the rapid diagnosis of blood-borne pathogens.

It is another object to provide on-line instrumentation capable of rapid spectrophotometric blood typing.

It is an additional object to provide such instrumentation having at least 2 nanometer resolution.

It is yet a further object to provide a technique capable of quantifying bodily fluid components, and, more particularly, blood components.

It is yet another object to provide portable instrumentation capable of performing on-line analysis of bodily fluid components at remote locations.

It is yet an additional object to provide a method and apparatus for characterizing platelets with regard to at least one of the factors of viability, contamination, and crossmatching.

It is a still further object to provide a method and apparatus for counting a component of blood, such as, but not limited to, white blood cells.

These and other objects are addressed by the apparatus and method of the present invention for a method for determining the type of a blood sample. The method comprises the steps of collecting a transmission spectrum of the blood sample over a predetermined wavelength range and, when appropriate, calculating an extinction spectrum for the blood sample.

The next step comprises comparing the extinction spectrum with a set of control spectra collected from control blood samples, each control sample having a known blood type. Typically this set of control spectra will comprise a database of spectra collected from a large number of samples in order to provide adequate statistics for the comparison. From this comparison the type of the blood sample under study can be determined.

In the preferred embodiment of the method of the invention, the predetermined wavelength range comprises generally the ultraviolet-to-visible wavelength range, from 180 to 900 nm.

The apparatus of the present invention comprises means for performing the above-listed steps. In a particular embodiment, the spectrum collecting means comprises a spectrophotometer.

An additional embodiment of the present invention is a method for detecting the presence of a substance in a bodily fluid sample, the substance having a size in the range of generally 0.01 to 20 µm. Exemplary substances and particles that could be of interest to detect include, but are not limited to, hemoglobin, bilirubin, red blood cell antigens, microorganisms, and viruses.

The method of this embodiment comprises the steps of collecting a transmission spectrum over a predetermined range of wavelengths of the fluid sample. Next the transmission spectrum, or the corresponding extinction spectrum, is deconvoluted to obtain the number of particles in the sample, the particle size distribution, and a chemical composition for the sample.

The extinction spectrum and the particle size distribution are then compared with, respectively, a control spectrum and a control particle size distribution for the substance. From these comparisons it can then be determined whether the organism to be detected could be present in the sample.

An alternate method for determining the type of a blood sample of the present invention comprises the steps of mixing a blood sample with an antiserum corresponding to a known blood type and then collecting a transmission spectrum of the mixture over a predetermined wavelength range, typically with the use of a spectrophotometer. Then an absorbance spectrum is calculated from the transmission spectrum for the mixture. The absorbance spectrum is then compared with a control spectrum collected from a control blood sample. From this comparison it can be determined whether an agglutination reaction between the blood sample and the antiserum has occurred. The presence of such an agglutination reaction is indicative of whether the type of the blood sample matches the corresponding antiserum type.

In practice a plurality of these studies would typically be undertaken simultaneously with a full range of antisera for positively determining the ABO and Rh type of the sample.

A related embodiment of the present invention comprises a method and apparatus for determining platelet viability in a stored sample. In a first subembodiment the method comprises the steps of collecting a transmission spectrum of a platelet-containing fluid sample over a predetermined wavelength range and calculating from the transmission spectrum an extinction spectrum for the sample. The extinction spectrum is then compared with a set of control spectra collected from a set of control samples having a range of viabilities. Finally, the viability is determined from the comparison.

The apparatus for carrying out this method can comprise either a spectrometer for collecting uv-vis transmission or reflectance spectra and/or a multiangle/multiwavelength optical bench. In either case, reflectance or backscattering measurements can be performed on a sample bag without invading the bag, or an aliquot can be removed for analysis. The analysis of the data thus obtained is performed using light scattering theory and spectral deconvolution techniques similar to those previously described.

In a second subembodiment platelet viability is determined using a method comprising the steps of positioning an indicator dye system whose spectrum (uv-vis or fluorescence) is sensitive to changes in pH on the inside of a container holding the fluid sample, typically a plasma bag. Next the color spectra of the pH indicator is spectrophotometrically determined, and the pH is calculated from the corresponding calibration of the indicator used. Finally, from the pH the viability of the sample is determined using known acceptable pH values for platelet bags. In some instances, by proper selection of the indicator dye, it may be possible to identify visually the changes in pH and therefore the platelet viability by comparison with a color code similar to that used for litmus paper.

Another embodiment of the present invention is directed to detecting contamination, such as bacterial contamination, in a blood sample, such as in plasma. In this application the contaminant typically will have a size generally in the range of 10 nm to 20 µm. The method comprises the steps of illuminating a volume portion of the sample, wherein the light energy is provided over a predetermined broadband wavelength range. A light energy spectrum is sensed at a plurality of observation angles corresponding to the broadband wavelength range emerging from the sample volume portion at the plurality of angles. In the multiangle/multiwavelength setup typically used for this application, the measurements are taken simultaneously, although this is not intended as a limitation.

The light energy spectrum is then transduced into a signal representative of an intensity spectrum as a function of wavelength for each observation angle. Next the combined scattering and absorption spectra are determined from the signal at each observation angle. From these spectra the particle characteristics are calculated and compared with a set of predetermined particle properties. From this comparison it is determined whether a contaminant is present in the sample.

Yet another embodiment of the present invention is a method and apparatus for cross matching platelet units, which is required for patients who are refractory to routine platelet transfusions. In this method a sample of plasma from a patient is obtained and mixed with a donor platelet sample. Then a transmission spectrum of the mixture is collected over a predetermined wavelength range. An aggregation state is then determined from the analysis of the combined absorption and scattering present in the sample. The platelet compatibility is then determined from the aggregation state.

The present invention also has use in quantifying a particular component of a blood or in another bodily fluid sample. An example of this embodiment is determining a white blood cell count in a plasma sample. The method comprises the steps of collecting a transmission spectrum of the plasma sample over a predetermined wavelength range. The transmission spectrum is then compared with a set of control spectra representative of a range of concentrations of the particle component of interest. The concentration of the particle can then be determined from the comparison.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
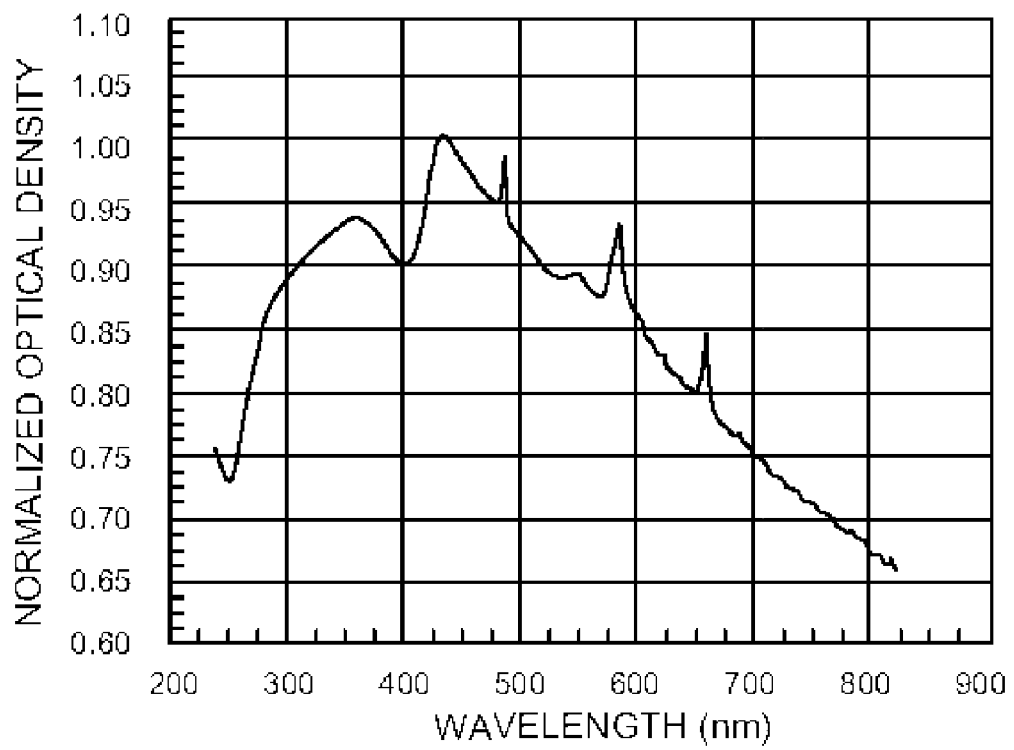
FIG. 1 shows a normalized optical density spectrum of a representative sample of A negative whole blood in phosphate buffered saline.
Figure 2:
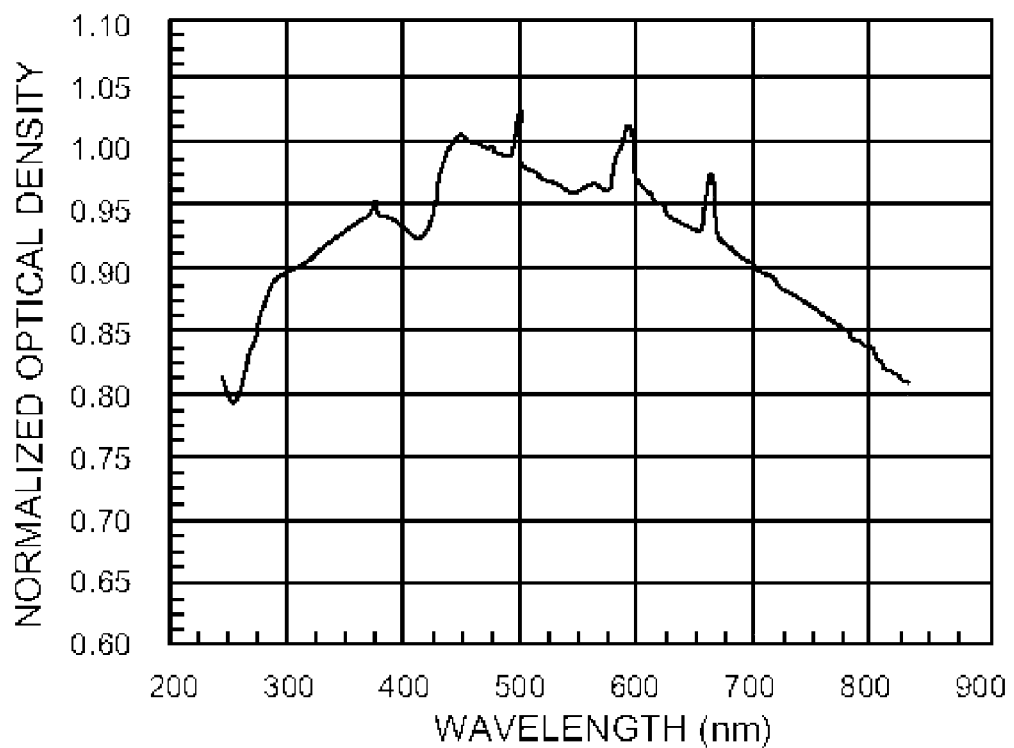
FIG. 2 shows a normalized optical density spectrum of a representative sample of O positive whole blood in phosphate buffered saline.
Figure 3:
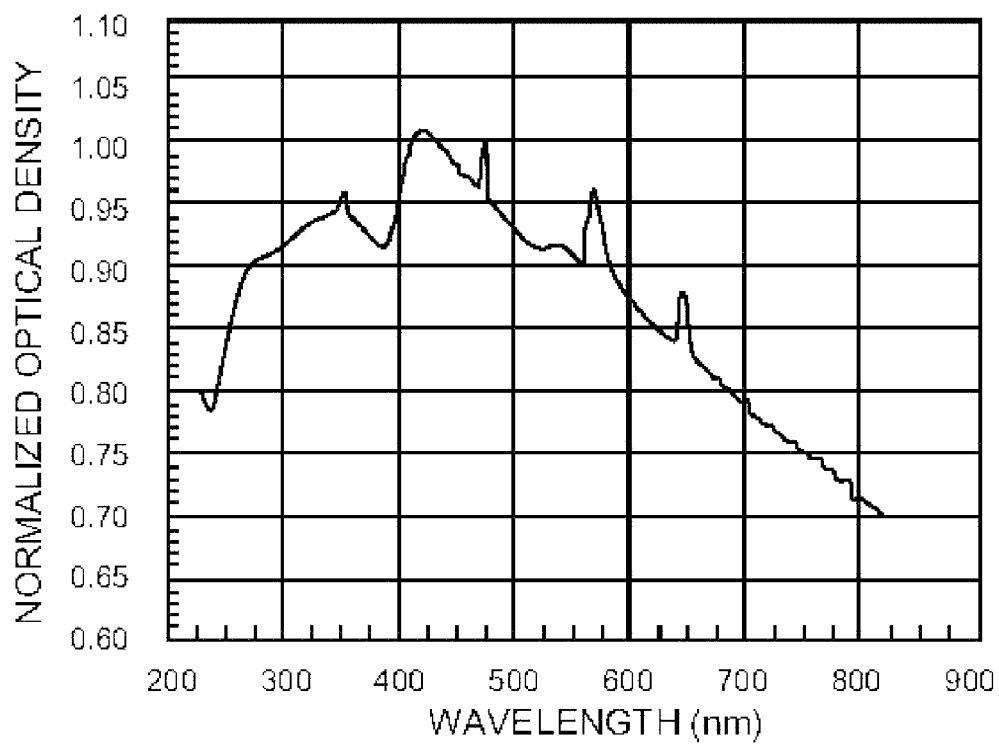
FIG. 3 shows a normalized optical density spectrum of a representative sample of AB positive whole blood in phosphate buffered saline.
Figure 4:
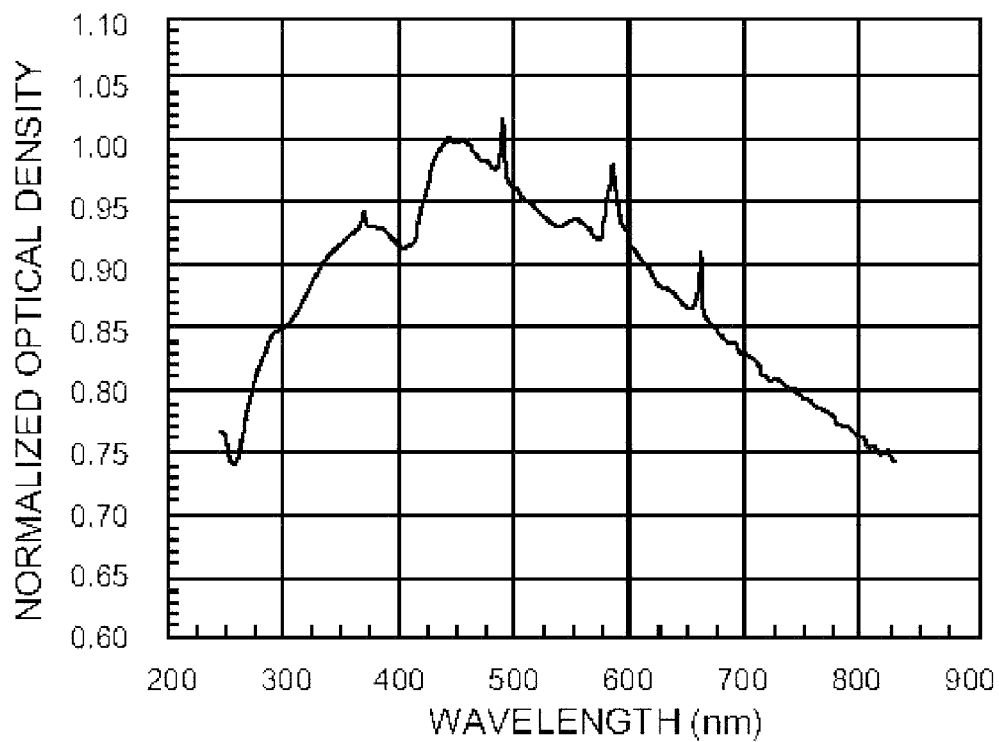
FIG. 4 shows a normalized optical density spectrum of a representative sample of B positive whole blood in phosphate buffered saline.

A description of the preferred embodiments of the present invention will now be presented with reference to FIGS. 1-15.

THEORETICAL BACKGROUND AND DEVELOPMENT

Dilute Dispersions

The optical spectral extinction of a particle dispersion such as whole blood or a sample of blood components contains information that, in principle, can be used to estimate the particle size distribution (PSD) and the chemical composition of the suspended particles. A large number of techniques for the estimation of the PSD from transmission spectra have been reported (van de Hulst, 1957; Kerker, 1962; Rousseau, 1984). Unfortunately, most of these techniques require that either the form of the PSD be known a priori, or that the shape of the PSD be assumed (Zollars, 1980; Melik and Fogler, 1983). More recently, regularization techniques (Towmey, 1979; Golub, 1979; Tarantola, 1987), applied to the solution of the transmission equation (Elicabe and Garcia-Rubio, 1990), have been demonstrated to yield the correct particle size distribution of the large variety of polymer lattices (Brandolin and Garcia-Rubio, 1991) and protein aggregates (Garcia-Rubio et al., 1993), SiO$_2$ particles (Chang et al., 1995), and microorganisms (Garcia-Rubio and Rose, unpublished). The present inventors have devised a technique for determining a discretized particle size distribution from transmission spectra. The equations providing the theoretical framework are developed from a relation between the transmission as a function of wavelength $\tau(\lambda_0)$ and the normalized particle size distribution $f(D)$:

$$\tau(\lambda_0) = N_p (\pi/4) \int_0^\infty Q(\lambda_0, D) D^2 f(D) dD, \qquad (1)$$

where D is the effective particle diameter, $Q(\lambda_0,D)$ corresponds to the Mie scattering coefficient, and $N_p$ is the number of particles per unit volume. Equation (1) can be written in matrix form by discretizing the integral with an appropriate quadrature approximation (Elicabe and Garcia-Rubio, 1990):

$$\tau = A + \in, \quad (2)$$

where $\in$ represents both experimental errors and errors due to the model and the discretization procedure (Elicabe and Garcia-Rubio, 1990). The regularized solution to Eq. (2) is given by:

$$(\gamma) = (A^T A + \gamma H)^{-1} A^T_\tau, \quad (3)$$

where H is a covariance matrix that essentially adaptively filters the experimental and the approximation errors ($\in$), and $\gamma$ is the regularization parameter estimated using the generalized cross-validation technique (Golub et al., 1979). This technique requires the minimization of the following objective function with respect to $\gamma$ (Golub et al., 1979):

$$V(\gamma) = m |[I - A(A^T A + \gamma H)^{-1}] \tau|^2 / Tr\{[I - A(A^T A + \gamma H)^{-1}] A^T\}^2 \quad (4)$$

A simultaneous application of Eqs. (3) and (4) to the measured transmission spectra yields the discretized particle size distribution. Using the appropriate optical properties of the materials, the solution to Eqs. (3) and (4) will yield the relative proportions of particles with different chemical composition present in the sample. Note that all the parameters required for the calculation of particle size distribution are obtained from the data. The scattering corrected spectra can also be used for composition analysis and/or to fingerprint the absorption characteristics of the particles.

Concentrated Dispersions

The interpretation of reflectance measurements depends on the type of illumination and light collection system used. The radiation reflected is usually regarded as comprising two distinct parts: specular reflectance, which is governed by the Fresnel equation (Wolf and Born, 1964), and diffuse reflection, which comes about from the penetration of a portion of the incident flux into the interior of the sample (Wendlandt and Hecht, 1966; Kortum, 1969). Part of this radiation is returned to the surface of the sample following partial absorption and multiple scattering at the boundaries of the individual particles of which the sample is composed. The attenuation of the diffuse part of the reflection by absorption within the medium is given by the Bouguer-Lambert law:

$$I(d) = I_0 \exp(-\epsilon d) \quad (5)$$

where $\epsilon$ is the molar extinction coefficient and d is the mean penetration layer thickness. In contrast with specular reflection, which can be adequately described from Fresnel's laws, no general theory is yet available that can be considered fully applicable to the diffuse reflection case. Nevertheless, in many instances, it has been shown that Lambert's cosine law for the reflected intensity can be applied (Wendlandt and Hecht, 1966; Kortum, 1969):

$$B(\alpha, \theta) = \left(\frac{I_0}{\pi'}\right) \cos\alpha \sin\theta \quad (6)$$

where $B(\alpha, \theta)$ corresponds to the radiation strength reflected in the direction opposite to the incident flux, $I_O$ is the radiation strength, $\alpha$ is the angle of incidence, and $\theta$ is the angle of observation. There are several approaches to the problem of describing the behavior of light in diffusing in dense media (Ishimaru, 1978). The most widely used description, because of its simplicity and effectiveness, are the flux models first proposed by Shuster and further developed by Kubelka and Munk (Wendlandt and Hecht, 1966; Kortum, 1969).

Under the assumption of a slab or medium comprising uniform and randomly distributed particles whose dimensions are much smaller than the thickness of the slab (FIG. 9), and the approximation of the medium having infinite lateral extension, so that edge effects can be neglected, it is possible to formulate a set of differential equations for the calculation of the radiation flux in the direction of incidence (I) and in the direction opposite the incident flux (J). Furthermore, if the medium under consideration is assumed to be isotropic (i.e., the Lambert cosine law applies), the differential equations can be formulated as:

$$dI = -(k+s)Idx + sJdx \quad (7)$$

$$dJ = +(k+s)Jdx + sIdx \quad (8)$$

where $k = 2\epsilon$ and $s = 2\sigma$; $\sigma$ corresponds to the scattering coefficient, and $\epsilon$ to the absorption coefficient. Equations (7) and (8) are strictly valid only for the case of ideal diffusion of light in the layer under consideration. Ideal diffusion can be achieved, in some cases, with parallel light illumination, and certainly it is approached in the case of diffuse incident radiation. These equations have the advantage that they can be readily integrated for a variety of boundary conditions and extended for cases where more than one layer is present. The general solution is:

$$I = A(1-\beta)\exp(\kappa\chi) + B(1+\beta)\exp(-\kappa\chi) \quad (9)$$

$$J = A(1+\beta)\exp(\kappa\chi) + B(1-\beta)\exp(-\kappa\chi) \quad (10)$$

$$\kappa = \sqrt{k(k+2s)}; \beta = \sqrt{\frac{k}{k+2s}} \quad (11)$$

A and B are the integration constants, which depend upon the boundary conditions. k is the microscopic absorption coefficient, and s is the microscopic scattering coefficient. The appropriate boundary conditions, with $\chi$ the sample depth, are:

$$I = I_O \text{ at } \chi = 0; I = I_{\chi = d}, J = 0 \text{ at } \chi = d \quad (12)$$

Solving for A and B, it is possible to write the formulae for the transmittance (T):

$$T = \frac{I_{\chi = d}}{I_0} = \frac{4\beta}{(1+\beta)^2 \exp(\kappa\chi) - (1-\beta)^2 \exp(-\kappa\chi)} \quad (13)$$

and the diffuse reflectance R of the layer, $$R = \frac{J_{\chi = 0}}{I_0} = \frac{(1-\beta^2)[\exp(\kappa\chi) - \exp(-\kappa\chi)]}{(1+\beta)^2 \exp(\kappa\chi) - (1-\beta)^2 \exp(-\kappa\chi)} \quad (14)$$

If an infinite layer thickness is considered (d→∞), T→0, and the reflectance ($R_\infty$) becomes:

$$R_\infty = \frac{(1-\beta)}{(1+\beta)}; \text{ alternately, } \frac{(1-R_\infty)^2}{2R_\infty} = \frac{k}{s} \quad (15)$$

Equation (15) is commonly referred to as the Kubelka-Munk equation or the Kubelka-Munk remission formula.

Notice that Eq. (15) is a function only of the absorption and scattering coefficients. However, these coefficients are, in general, functions of the wavelength. By taking the limit of Eq. (14) when s→0, it can be shown that the absorption coefficient k in Eqs. (7)-(15) bears the same significance as that customarily employed in transmission spectroscopy [i.e., Eq. (13) reduces to the Beer-Lambert law]. Unfortunately, the scattering coefficient s does not have a direct translation. The scattering coefficient in the Kubelka-Munk theory and, for example, the Mie scattering cross section are not identical. In Mie theory, any alteration in the direction of the incident wave not caused by refraction is considered scattering, while in the Kubelka-Munk theory the radiation is only regarded as scattered when it is backward reflected (Kortum, 1969). Nevertheless, because of the multiple scattering events within the medium, even the backscattering coefficient predicted by Mie theory cannot be directly related to the Kubelka-Munk scattering coefficient (Ishimaru, 1978).

Numerical solutions to the radiation transfer equation (Ishimaru, 1978; Britton, 1986) allow a better formulation to the problem of interpretation of the absorption and scattering coefficients, but at this point analysis of these formulations will detract from the current objective, which is the identification and understanding of the main variables affecting the measurements.

The most important conclusion from the above discussion is that if it can be shown that the Kubelka-Munk absorption coefficient is proportional to the Beer-Lambert absorption coefficient, then the additivity of the contributions from the chromophores present is likely to hold, and that given this approximation, the scattering coefficients can be estimated in the context of a suitable calibration. For the solution resulting from the conditional estimation problem, the use of Eqs. (13)-(15) has the advantage of simplicity and the possibility of using independent measurements of the absorption coefficients. Furthermore, since relative to the wavelength of uv-vis radiation a platelet bag or blood sample can be approximated as an infinite medium, Eq. (15) can be used to define the structure of the calibration model to be implemented with a sensor.

An advantage of the direct proportionality between the Kubelka-Munk and the Beer-Lambert absorption coefficients is that it is well known that the Beer-Lambert absorption coefficient can be approximated as a weighted sum of the absorption coefficients of all the chromophoric species present:

$$\epsilon(\lambda) = \sum_{n}^{N} \epsilon(\lambda, n) p(n) \qquad (16)$$

where p(n) is the weight fraction of the nth chromophore. Clearly, Eq. (16) can be used in conjunction with Eq. (8) to estimate the Kubelka-Munk absorption coefficient, if the absorption coefficient of the chromophores present are known. This implies that the measured absorption coefficient $\in(\lambda,n)$ for the different types of hemoglobin and other analytes will constitute the basis set for the deconvolution of the measured reflectance spectra.

pH Measurement Using Uv-Vis Spectroscopy

The response of a sensor is determined by the dissociation equilibrium of an immobilized dye, its interaction with the polymer matrix, and the ionic strength of the medium. The pH membrane is made up of an indicator dye immobilized in a polymer matrix (such as cellulose). The indicator dye can be chemically bonded to or physically confined within the polymer matrix. The purpose of immobilization is to provide the indicator dyes from leaching out, which is especially important in biomedical applications.

The indicator possesses chromophores whose absorptions change according to the pH of the surroundings. The reaction involves an equilibrium between the immobilized dyes and hydrogen ions: $H^+ + A^- \sqrt{} HA$, where HA and $A^-$ are the protonated and the dissociated forms of the dyes, respectively. The equilibrium constant, $K_a$ is represented as:

$$K_a = \frac{[H^+][A^-]}{[HA]} \qquad (17)$$

The Henderson-Hasselbach equation establishes the relationship between the spectrophotometrically measured concentrations and the pH of the solution:

$$pH = pK_a + \log\frac{[A^-]}{[HA]} = pK_a + \log\frac{\alpha}{1-\alpha} \qquad (18)$$

Figure 12:
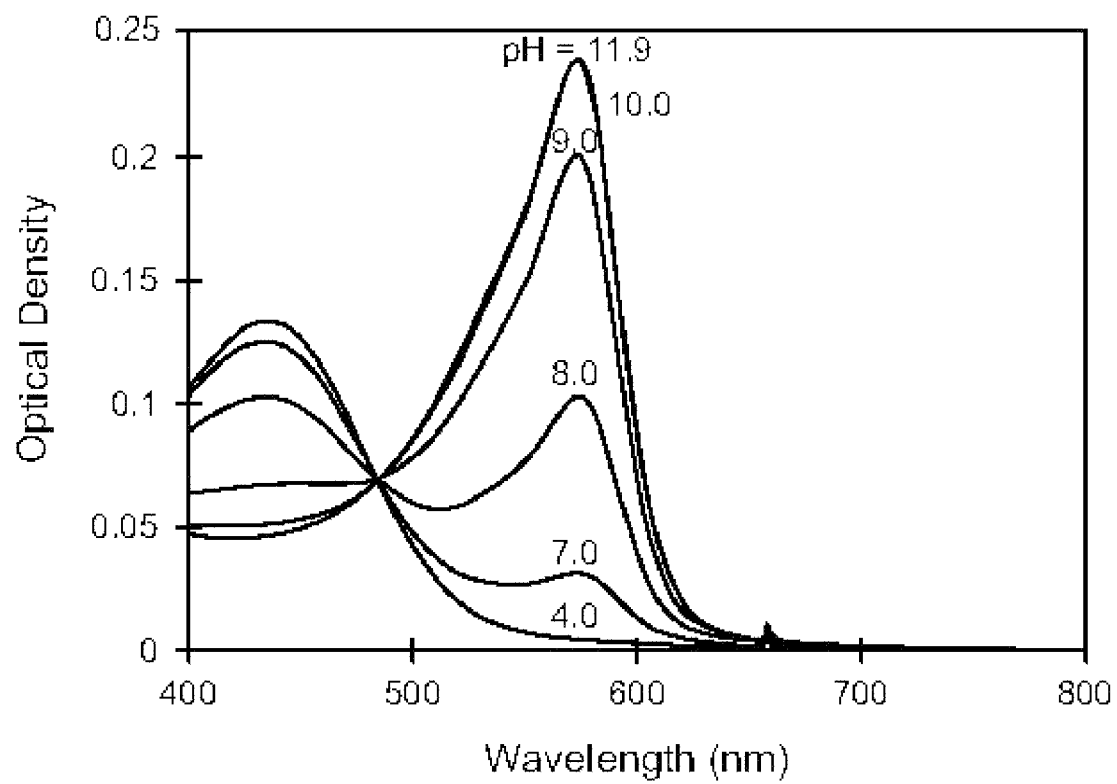
FIG. 12 illustrates the effect of pH on the optical density of phenol red dye.

The pH is determined by the relative fraction of the dissociated and the protonated forms of the dye, which are optically detectable. In transmission measurements, the concentration is related to the absorption by the Beer-Lambert law:

$$A_i = C_i \epsilon_i l \qquad (19)$$

where $A_i$ is the absorption of species i, $C_i$ is the concentration, $\epsilon_i$ is the extinction coefficient, and l is the pathlength the light travels. Under the assumption of additivity of chromophores, any intermediate pH value will result in a unique absorption spectrum, as can be seen in FIG. 12. For simple acids and bases, the pH is determined by the relative fractions of the acidic and basic forms of the dye, which are intrinsic properties of the dye and are independent of the concentration and pathlength.

Because different pH ranges may need to be measured, different indicator dyes have been investigated by Edmonds et al., and thus the $pK_a$ can be predicted and estimated very well using the current method developed by Chang and Garcia-Rubio (1996). As a result, the pH can be measured to within 0.001 pH unit. The newly developed theory (Chang, 1996) accounts for the chemical structure of the dye, temperature, ionic strength, film thickness (including swelling), and the buffering capacity of the matrix.

Blood Typing Apparatus and Method Using Whole Blood

Figure 7:
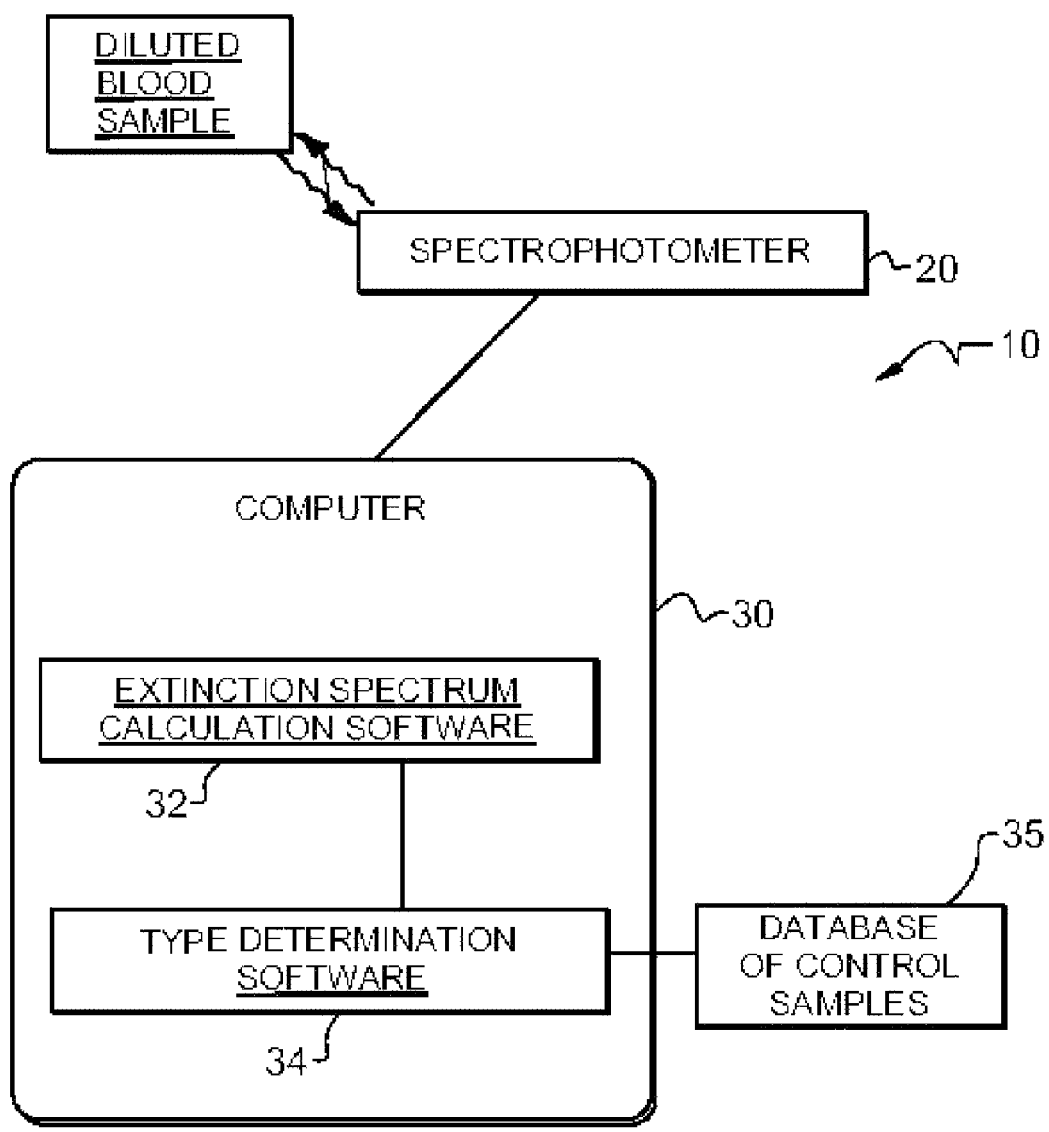
FIG. 7 is a block diagram of the system configuration.

The apparatus 10 and method of using same for determining the type of a blood sample are depicted in FIG. 7. This embodiment can be performed with portable equipment, and hence can serve as a rapid, on-line technique.

In the particular embodiment of the method to be treated herein, whole blood is used for the blood samples. Due to the optically dense nature of whole blood, considerable dilution is required prior to quantitative spectrophotometric measurements to reach a linear range of the spectrophotometer 20. Typically this is accomplished by serial dilution of the sample with phosphate buffered saline. The dilution in this embodiment consisted of first a 1:50 whole blood—to —PBS dilution followed by an additional 1:20 dilution of this solution into PBS. This resulted in a red blood cell count ranging from 3900 to 4100 per microliter and an optical density of 0.1 to 1.0 absorption units, which is within the linear range of the instrument. This series of dilutions typically will result in a solution that is in the linear range of the spectrophotometer used.

Using a spectrophotometer 20, such as a Hewlett Packard 8452A Diode Array Spectrophotometer, a transmission spectrum of the blood sample is collected over a predetermined wavelength range. In the preferred embodiment the predetermined wavelength range comprises generally the ultraviolet-to-visible (uv/vis) wavelength range, specifically, generally 180 to 820 nm, with a 2 nm resolution.

Figure 8:
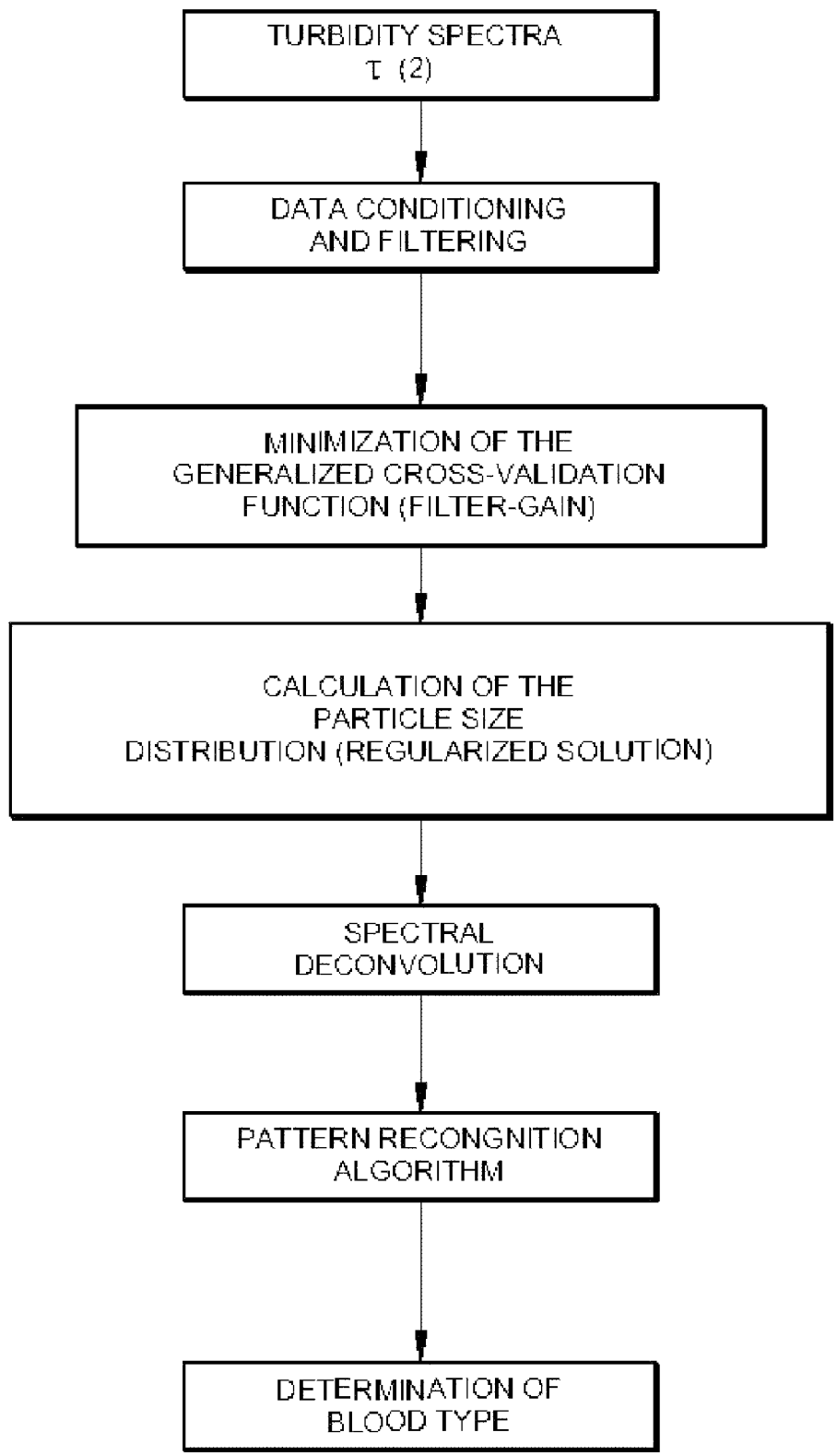
FIG. 8 is a flow chart of the data analysis method.
Figure 9:
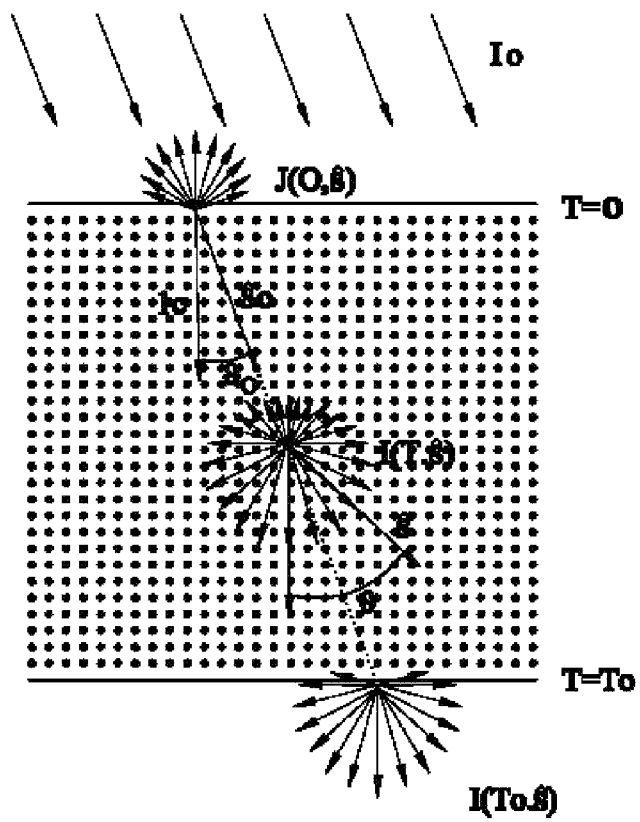
FIG. 9 is a schematic diagram of a slab containing particles imbedded in a medium with refractive index $n_0$. The illumination ($I_0$) is from the perpendicular direction. The reflected light J(0,s) is in the direction opposite to the illumination.

Using the transmission spectrum thus obtained, which is recorded on a computer 30 such as a Hewlett Packard Vectra 286/12 personal computer, an extinction spectrum is calculated using software developed by the inventors (see FIG. 8). This calculation further entails normalizing intensity effects due to the concentration of red blood cells in the blood sample.

In order to calculate the error associated with the extinction spectra, five additional dilutions of the sample were measured. The first two dilutions involved addition of solvent to the cuvette (the measuring vial) followed by thorough mixing and measurement. The final two dilutions involved removal of a portion of the solution from the cuvette, followed by addition of solvent, thorough mixing, and measurement.

A database set of control spectra collected from control blood samples was initially compiled by choosing samples of a specific gender and age range that are free of disease as judged by normal blood bank screening procedures. The control blood samples each have a known blood type. A complete database is contemplated as containing samples of both genders and a wide range of ages. The measurements reported herein are limited to females in the age range of 17 to 43 years. The broad age range is preferred in order to accumulate information on rarer blood types, which make up a small percentage of the blood donor population and are difficult to obtain for analysis. The samples obtained include blood from the major eight blood types: A, B, AB, and O, both Rh positive and negative.

Figure 5:
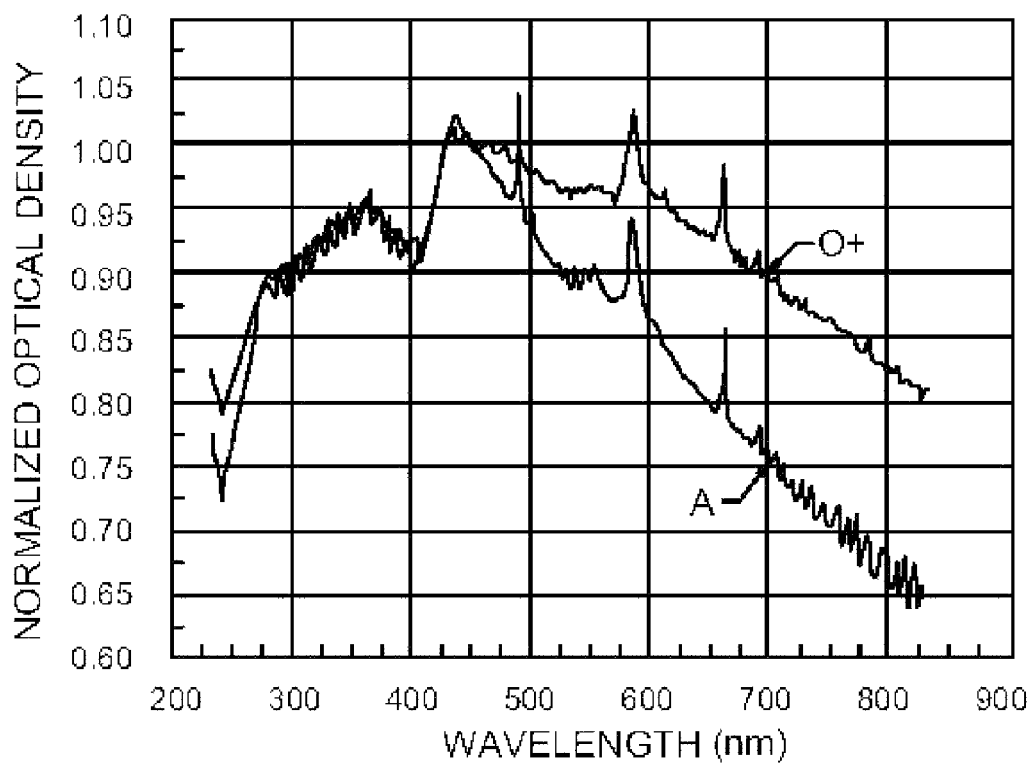
FIG. 5 shows typical 95% confidence intervals associated with the normalized optical density spectra of two different blood samples. The thickness of the lines is indicative of the reproducibility of the experimental protocol.

In FIGS. 1-4, the normalized extinction spectra for representative samples of four of the eight different blood types are shown. FIG. 5 has the typical 95% confidence intervals superimposed on two different spectra to indicate the level of precision and the reproducibility of the experimental protocol.

Typing of a sample can then be performed by comparing the extinction spectrum with the set of control spectra and determining from the comparison the type of the blood sample. Specifically, the typing is based on spectral differences that appear throughout portions of both the ultraviolet and visible range. At present the origin of these differences is unknown, but it may be due to intrinsic absorption differences at the molecular level or scattering differences brought about by either subtle variations in cell surface characteristics, cell shape, or state of aggregation.

A comparison of the spectra taken from samples of whole blood for different blood types (FIGS. 1-4) clearly indicates that, although the spectra are generally similar in that they contain the same peaks and troughs, the underlying structure and the relative peak intensities are consistently and significantly different. Furthermore, a statistical analysis of the samples also suggests that the blood types are spectrally distinguishable. Therefore, it can be concluded that the uv/vis portion of the spectrum contains sufficient information for the statistical identification and classification of blood types.

In order to test one aspect of the origin of differences in samples of different blood types, transmission spectra were collected on lysed red blood cell samples. The procedure for this test included dilution with two different hypotonic solvents, 0.3 and 0.4% buffered NaCl, chosen to be sufficiently hypotonic to lyse the red blood cells.

Figure 6:
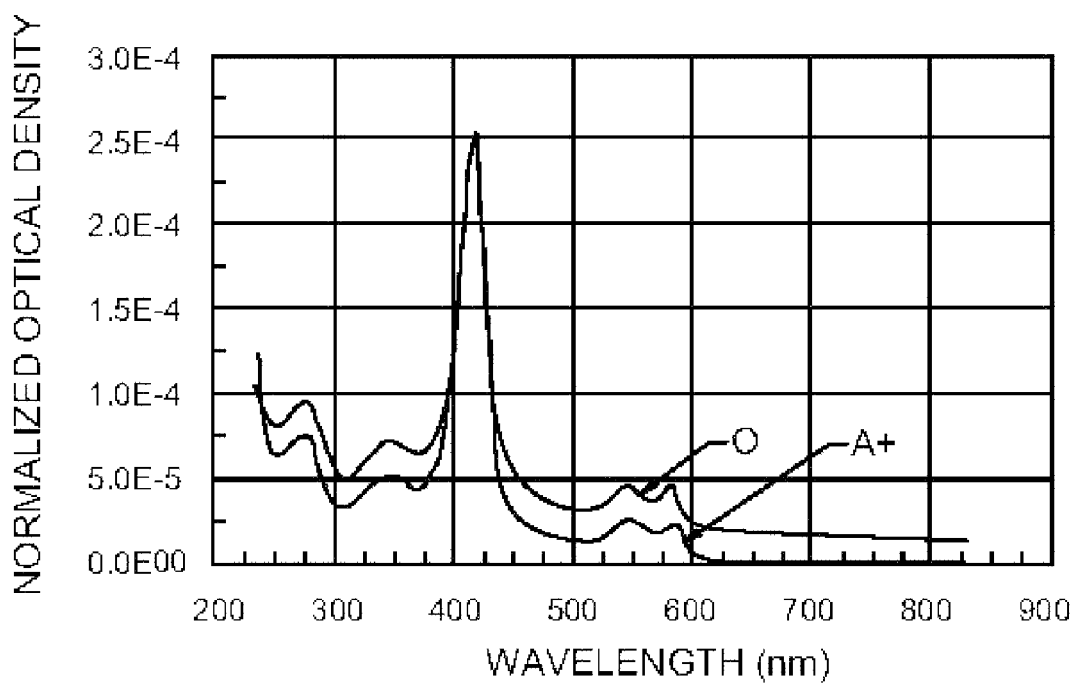
FIG. 6 shows optical density spectra of lysed O negative and A positive red blood cells. Cells were lysed by suspension in hypotonic saline solution (A positive in 0.3% and O negative in 0.4% buffered NaCl).

FIG. 6 shows spectra taken from two lysed blood specimens, specifically 0 negative and A positive types. A comparison of FIGS. 1-4 with the spectra of the red blood cell components in FIG. 6 shows clear and significant differences between these samples. It can be noted that the spectra for the lysed cell samples are quite similar to each other; that is, the number of peaks, peak positions, and relative intensities are the same for the two distinct blood types once they have been lysed. Therefore, the differences observed between blood types appear to be due to cell size or one or more components of the whole cell structure rather than gross chemical composition. Similar conclusions can be drawn from spectra collected from plasma, which are almost identical regardless of the differences in the whole blood type from which they came.

A further aspect of the present invention is an apparatus for determining the type of a blood sample. The apparatus in general comprises means for performing the steps of the above-discussed method. In the preferred embodiment, the apparatus includes a spectrophotometer for collecting spectra in the predetermined wavelength range of generally 180 to 800 nm with a resolution of 2 nm, the sample having been sufficiently diluted to reach a linear range of the spectrophotometer.

Additionally, the calculating means comprises software means resident in a computer.

Detection of a Substance in a Bodily Fluid Sample

In yet another embodiment, a method is provided for detecting the presence of a substance in a bodily fluid sample, the substance having a size in the range of generally 0.01 to to 20 μm. Exemplary substances that could be of interest to detect include, but are not limited to, hemoglobin, bilirubin, red blood cell antigens, microorganisms, and viruses. The method generally comprises the steps of collecting a transmission spectrum over a predetermined range of wavelengths of the fluid sample and calculating from the transmission spectrum an extinction spectrum.

The method further entails deconvoluting the extinction spectrum to obtain a particle size distribution for the sample, as outlined in the above discussion on the transmission equations. The extinction spectrum and the particle size distribution are then compared with, respectively, a control spectrum and a control particle size distribution for the substance, and it can then be determined from the comparisons whether the particle to be detected is present in the sample. Another application includes a further step, to determine the quantity of the substance to be detected in the fluid sample from the particle size distribution.

In order to accomplish the foregoing, an additional series of databases must be compiled for each of the components of interest. A quantitative identification of the blood components and the generation of an adequate database allows for the subsequent identification of blood abnormalities such as those brought about by bacterial or viral infections by comparison with the spectral signature of normal blood, and by differences in the cell size distribution calculated from the same measurement.

For a more detailed characterization, these spectra can be further analyzed in conjunction with other currently employed technologies, such as dynamic light scattering, in order to estimate the number as well as the complete size distribution of the components of interest according to size and chemical composition.

Blood Typing with the Use of an Agglutination Reaction

In this embodiment of the blood typing method and apparatus, a standard agglutination reaction is undergone with dilute blood in a spectrophotometer. A ratio of antibody to red blood cells for ABO and Rh typing is similar to that used in prior art methods, such as used with an Olympus instrument.

Specifically, an EDTA specimen is centrifuged to obtain concentrated red blood cells. A 1:16 dilution of red blood cells is then made in normal saline. The concentration of this dilution is determined using, for example, an automated hematology analyzer, such as a Serono Baker 9010+.

Commercial antisera are diluted to a concentration that will yield microscopically positive agglutination when incubated with the corresponding antigen. An enhancing medium can be used to determine the presence of weak antigens, such as weak D. Equal volumes of diluted antisera and diluted red blood cells are added together and incubated at room temperature for approximately 1 minute. Then the specimen is diluted to read at an absorbance of approximately 1.0.

Figure 10:
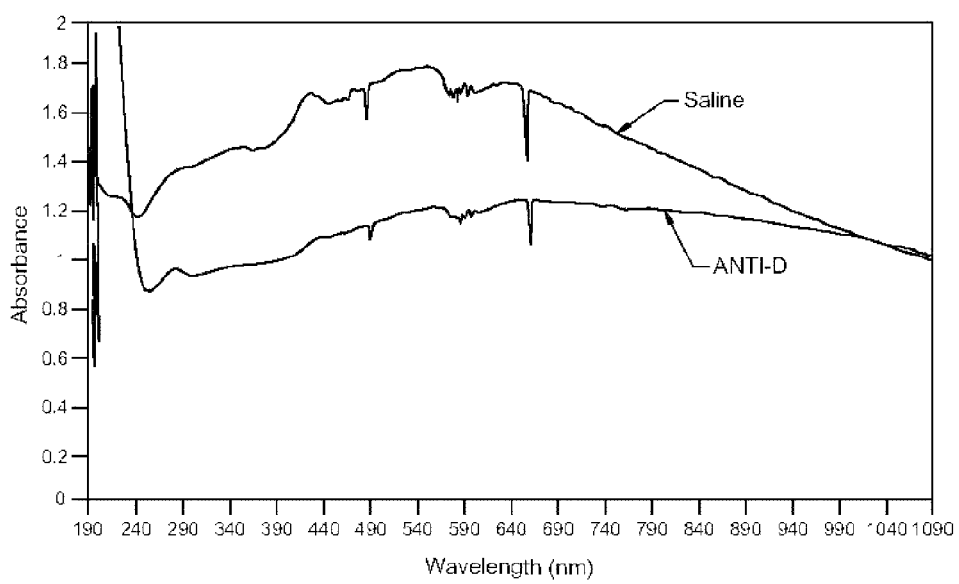
FIG. 10 is a normalized optical density spectrum for a control saline sample and a sample containing an antigen, here D, with the corresponding antiserum.

A difference in the spectra corresponding to a reaction between the red blood cells and the antisera can be seen (see FIG. 10). Spectra corresponding to the specimen and a control (lacking red blood cells) are normalized to a single wavelength. In this way it can be determined if subtle differences between spectra are due to differences in concentration between the test and control or to true differences between the curves.

The apparatus for this embodiment can comprise a spectrophotometer for collecting uv-vis transmission spectra or a multiangle-multiwavelength setup. Analysis is performed using light scattering theory and spectral deconvolution.

Platelet Viability

The viability of a sample containing platelets can be determined by two subembodiments of the present invention: using light scattering or using a pH indicator.

Light Scattering/Absorption Spectroscopy.

Platelets are known to change shape upon activation and to expel the contents of several cytoplasmic granules. A shape change from a thin disk to a spheroid can be monitored with the use of the above-discussed multiangle/multiwavelength spectrophotometer. The change in internal composition following the expulsion of the granule contents can be monitored with standard uv-vis spectrophotometry.

Figure 11:
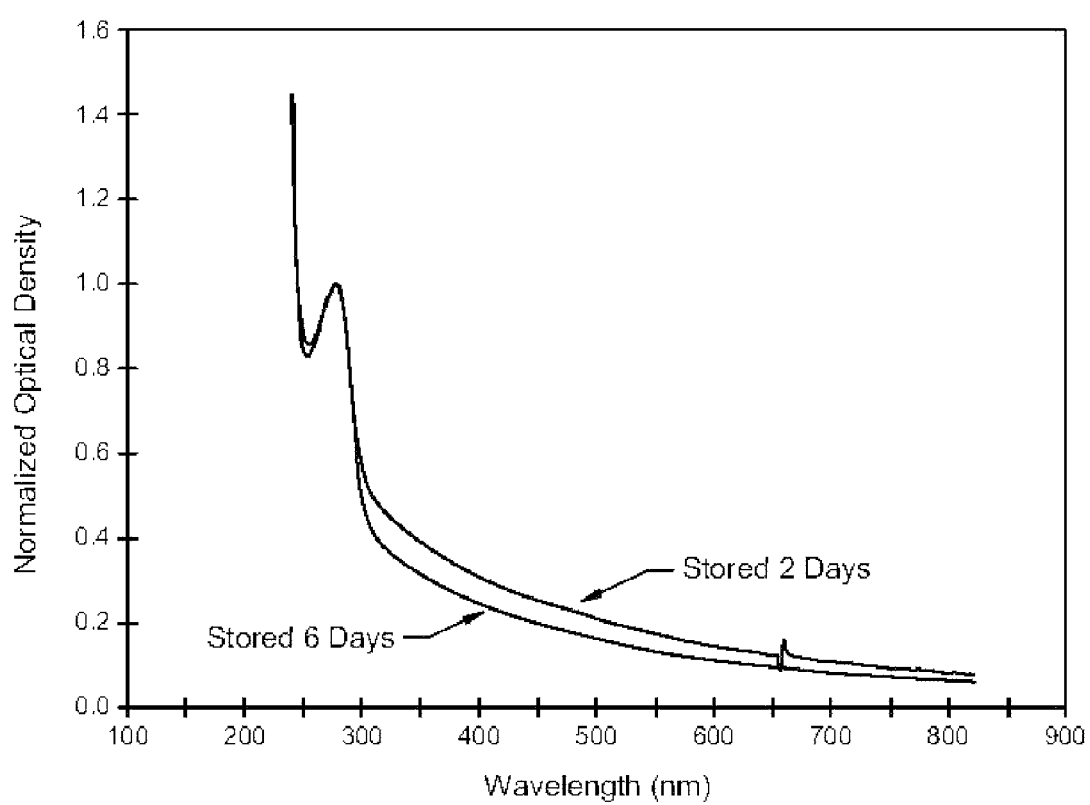
FIG. 11 illustrates two normalized optical density spectra for platelet-rich plasma stored for 2 and 6 days.

For the test the results of which are illustrated in FIG. 11, a platelet-rich plasma unit was stored for 1 day and divided into two aliquots using sterile techniques. A first aliquot was spectroscopically analyzed the next day (total storage time, 2 days), and a second aliquot was held and analyzed 4 days later (total storage time, 6 days) after the unit had expired.

For spectroscopic analysis, platelet-rich plasma was diluted to a concentration of approximately 0.65 mg/ml in a platelet buffer such as Plasmalyte A. A total of 5 dilutions prepared in the cuvette from the initial 0.65 mg/ml dilution were scanned from 190 to 820 nm, with 2 nm resolution, on a diode array spectrophotometer (Hewlett Packard, HP8452A). Alternatively, measurements can be taken with a multiangle/multiwavelength setup as described earlier.

The extinction spectra illustrated in FIG. 11 were generated from the 5 dilutions scanned for each aged aliquot. The spectra were normalized to the extinction coefficient at 280 nm to enhance spectral shape differences. The spectral differences observed for the fresh and expired samples of platelet-rich plasma are quantitative and are usable as an indicator of platelet viability.

The method may be carried out by taking reflectance measurements through a sample bag without directly sampling the unit, or a small aliquot can be removed, diluted, and analyzed spectroscopically.

pH Indicator.

In this subembodiment, a specially designed pH-sensitive indicator, which is nonbleeding and selected in accordance with a desired pH range (i.e., 4-9), is positioned inside the platelet sample bag. Typical indicators are phenol red (see FIG. 12) and cresol purple, although these are not intended to be limiting.

When in use, the indicator changes color as the pH of the unit changes; in the case of storage time effects, the pH drops with time, owing to the accumulation of metabolic products associated with aging.

In a particular embodiment the indicator color change may be visible upon visual inspection; alternatively, the color change may be detected photometrically, for example, with the use of a portable, fiber optic spectrophotometer.

A benefit of this method is that the pH can be determined without directly sampling the platelet-rich plasma unit.

Detection of Bacterial Contamination in Platelet-Rich Plasma

In a previously disclosed invention, entitled "Method and Apparatus for the Detection and Classification of Microorganisms in Water" (U.S. Pat. No. 5,616,457), a method and apparatus for detecting contaminants in water has been described.

Figure 13:
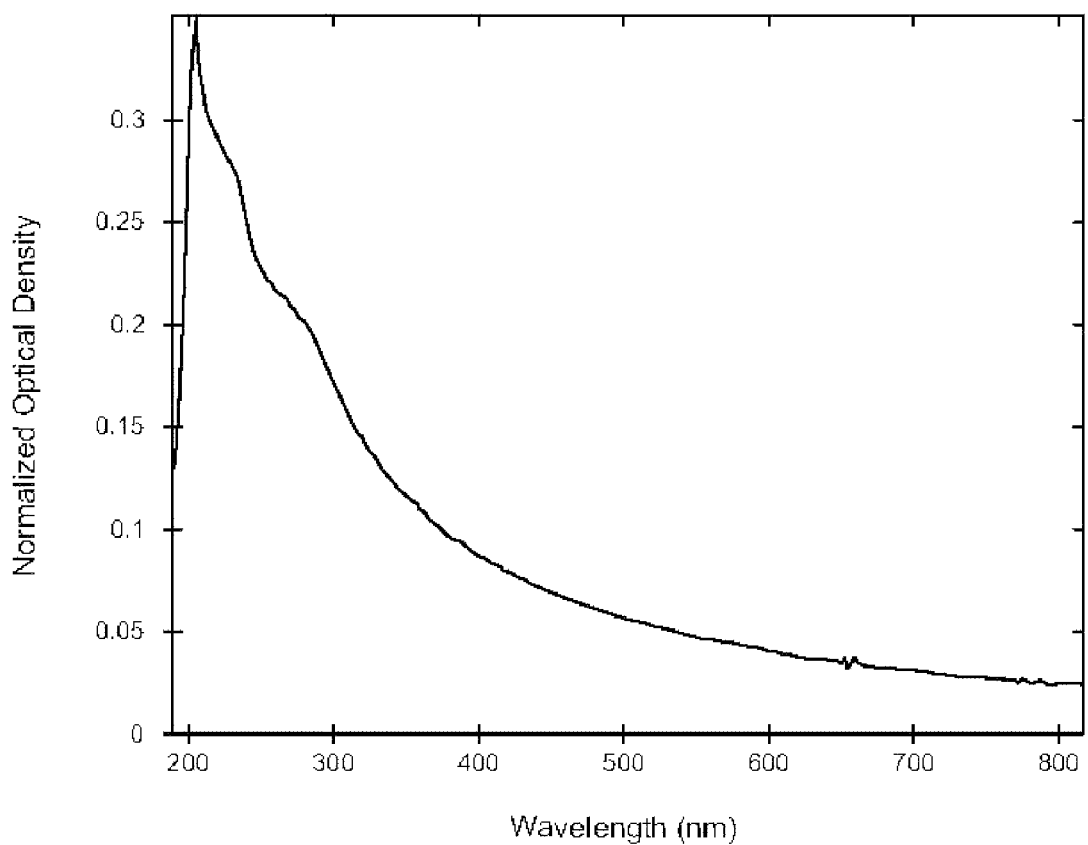
FIG. 13 is a normalized optical density spectrum of a sample containing *E. coli* bacteria.

In similar fashion, a contaminant can be detected in platelet-rich plasma, with the use of either a uv-vis spectrophotometer or a multiangle/multiwavelength setup. An exemplary spectrum for *E. coli* is shown in FIG. 13.

By analyzing the sample with uv-vis spectroscopy, the transmission spectrum can be deconvoluted in terms of the contributing species, including bacteria and other contaminants.

With the multiangle/multiwavelength instrument, the shape of a component can also be analyzed for and used to determine whether the sample is contaminated.

Spectra can be collected a reflectance measurements through the sample bag, or diluted samples can be analyzed with transmission measurements.

Spectroscopic Determination of Platelet Compatibility

A method and apparatus for cross matching platelet samples with patient plasma are provided by the present invention. Compatibility is determined spectrophotometrically with a single scan, with currently commercially available testing kit reagents.

In a particular embodiment, equal volumes of platelet-rich plasma, patient plasma, and a low-ionic-strength enhancing medium are incubated at 37° C. for 30 minutes. Indicator cells are then added, and the mixture is diluted to read at an absorbance of approximately 1.0.

The curves corresponding to the specimen and control (without the platelet-rich plasma) are normalized to a single wavelength. From a comparison of the curves it can be determined if differences between the curves are due to differences in concentration between the test and control or to differences between the curves.

Figure 14:
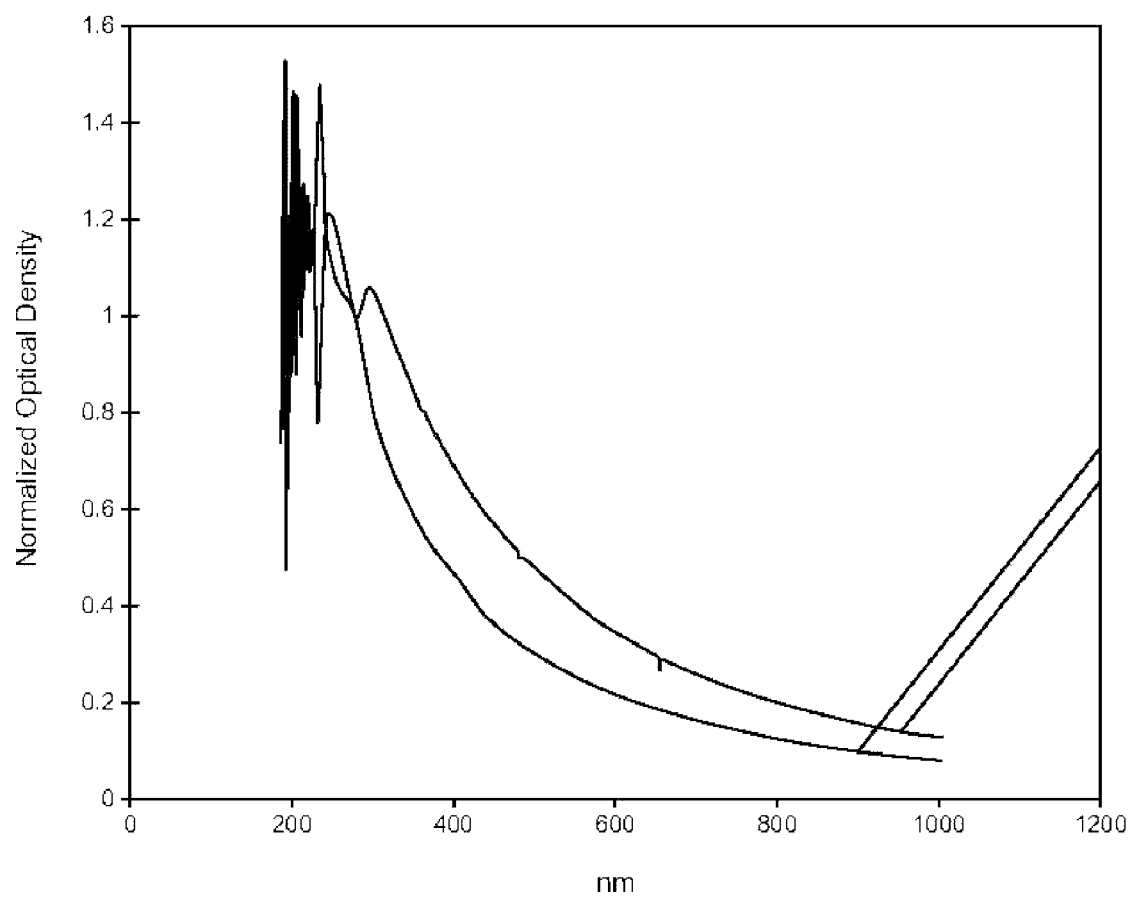
FIG. 14 shows a comparison of normalized optical density spectra collected for a patient test sample mixed with platelet-rich plasma containing compatible and incompatible platelets.

FIG. 14 is an exemplary set of curves for sample mixed with a compatible ("C") and an incompatible ("I") platelet unit.

Quantifying White Blood Cells in a Plasma Sample

In the method of the present invention, the specific optical properties of the components of the white blood cells are used to quantify white blood cells in a sample.

Figure 15:
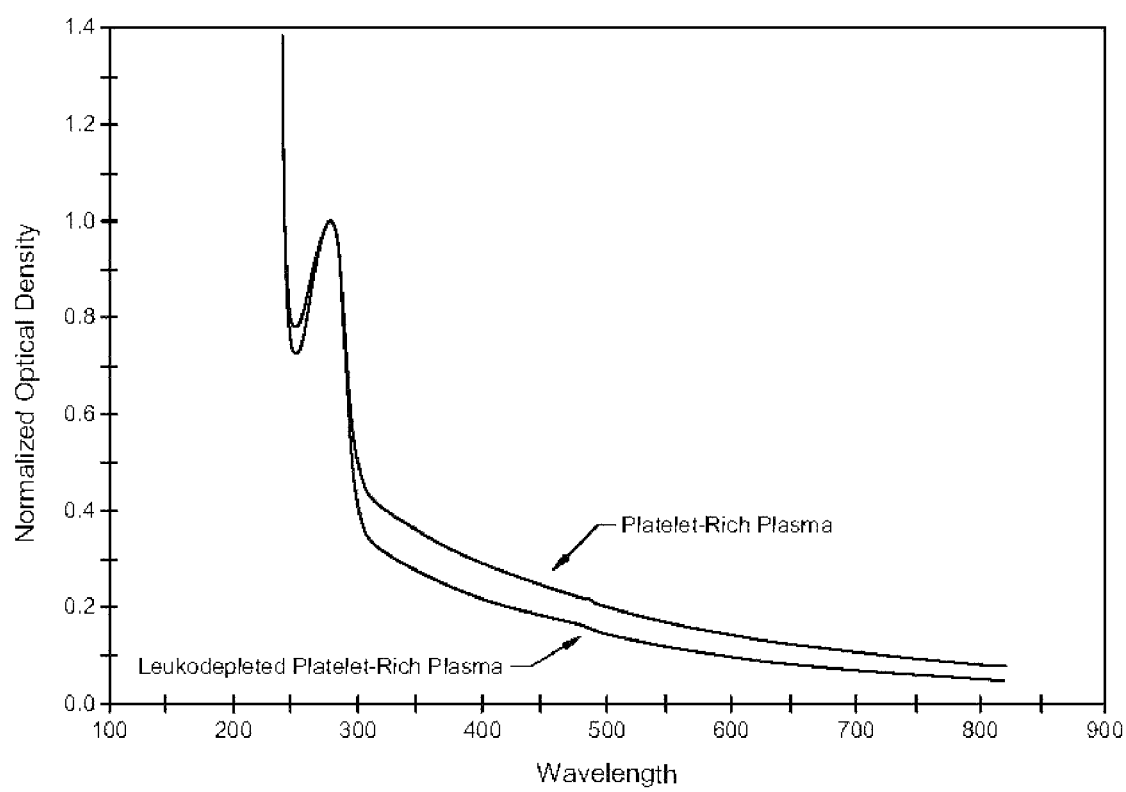
FIG. 15 contains normalized optical density spectra for platelet-rich plasma and leukodepleted platelet-rich plasma for counting white blood cells in a patient sample.

As illustrated in FIG. 15, a spectral difference can be seen between a platelet-rich plasma preparation and one comprising a leukodepleted platelet-rich plasma. Thus the white blood cell concentration can be monitored, even when the relative amounts present are small compared with that of other blood components such as platelets. For the exemplary curves shown, the initial concentration was 1% in PBS (phosphate-buffered saline).

Leukodepleted platelet-rich plasma is prepared from platelet-rich plasma by filtering the platelet unit with a leukocyte removal filter (PLF1, Pall Biomedical Products). This platelet preparation contained platelets, plasma, and a low level of red blood cells. The initial concentration used for leukodepleted platelet-rich plasma analysis was 1% in PBS.

For the exemplary curves in FIG. 15, a total of five dilutions were prepared directly in a cuvette from the initial dilutions of each platelet preparation. The samples were scanned from 190 to 820 nm on a diode-array spectrophotometer, although this type of spectrophotometer is not intended as a limitation. The extinction spectra shown were generated from the five dilutions scanned for each platelet preparation. The spectra were then normalized to the extinction coefficient at 280 nm to enhance spectral shape differences.

REFERENCES

Brandolin, A., Garcia-Rubio, L. H., Provder, T., Kohler, M. E., and Kuo, C., "Latex Particle Size Distribution from Turbimetry Using Inversion Techniques, Experimental Validation," ACS Symposium on Hyphenated Techniques in Polymer Characterization, Chicago, Aug. 22-27, No. 472 (1991), Chap. 2.

Britton, N. F., *Reaction Diffusion Equations and Their Applications to Biology*, Academic, New York (1978).

Campbell, D., and White, J. R., *Polymer Characterization Physical Techniques*, Chapman and Hall, London (1989).

Chang, S. H., "Modeling and Analysis of Fiber Optic Sensors," PhD Dissertation, Univ. South Florida (1996).

Chang, S. H., and Garcia-Rubio, L. H., "Modeling of Fiber Optic-Based Sensors," *Chemical, Biochemical, and Environmental Fiber Sensors* V2068, 11 (1993).

Chang, S. H., and Garcia-Rubio, L. H., "Determination of pH with Acid-Base Indicators: Feasibility Analysis for Optical Fiber Probes," *Talanta*, to be published.

Chang, S. H., Druen, S. L., and Garcia-Rubio, L. H., "Modeling and Analysis of Fiber Optic pH Sensors: Effect of the Ionic Strength," *SPIE Proc.*, 2388 (1995).

Chang, S. H., Koumarioti, Y., and Garcia-Rubio, L. H., "Turbidimetric Analysis of $SiO_2$ Particles," *J. Coll. Interface Sci.*, to be published.

Chang, S. H., Byrne, R. H., and Garcia-Rubio, L. H., "Comparison of Behavior of Indicator Dyes in Solution and Immobilized in a Polymer Matrix for pH Measurements," *Anal. Chem.*, submitted.

Elicabe, G., and Garcia-Rubio, L. H., "Latex Particle Size Distribution from Turbimetry Using a Combination of Regularization Techniques and Generalized Cross Validation," *Adv. Chem. Series* 227, Chap. 6 (1990).

Garcia-Rubio, L. H., "Averages from Turbimetry Measurements," *ACS Symp. Ser.* 332, 161 (1987).

Garcia-Rubio, L. H., "The Effect of Molecular Size on the Absorption Spectra of Macromolecules," *Macromol.* 20, 3070 (1987).

Garcia-Rubio, L. H., "Determination of the Absorption Coefficient of Proteins in the Presence of Protein Aggregates Using Turbimetry," *Chem. Eng. Comm.* 80, 193 (1989).

Garcia-Rubio, L. H., "Refractive Index Effects on the Absorption Spectra of Macromolecules," *Macromol.* 25, 2608 (1992).

Garcia-Rubio, L. H., "Multiangle-Multiwavelength Detection for Polymer Characterization," *ACS Symposium on Hyphenated Techniques in Polymer Characterization*, Chicago, Aug. 22-27, 1993.

Garcia-Rubio, L. H., and Ro, N., "Detailed Copolymer Characterization Using Ultraviolet Spectroscopy," *Can. J. Chem.* 63, 253 (1985).

Garcia-Rubio, L. H., Ro, N., and Patel, R. D., "UV Analysis of Benzoyl Peroxide Initiated Polymerizations and Copolymerizations," *Macromolecules* 17, 1998 (1984).

Golub, G. H., Heath, M., and Wahba, G., "Generalized Cross Validation as a Method for Choosing a Good Ridge Parameter," *Technometrics* 21, 215 (1979).

Ishimaru, A., *Wave Propagation and Scattering in Random Media*, Vols. I and II, Academic, New York (1978).

Kerker, M., Ed., *Electromagnetic Waves*, Pergamon, New York (1962).

Kortum, G., *Reflectance Spectroscopy*, Springer Verlag, Berlin-Heidelberg (1969).

Marquez, E., Bhethanabotla, V. R, and Garcia-Rubio, L. H., "Conformation Effects on the Absorption Spectra of Macromolecules," *Macromol.* 26, 479 (1993).

Melik, D. H., and Fogler, H. S., "Turbidimetric Determination of Particle Size Distributions of Colloidal Systems," *J. Coll. Interface Sci.* 92, 161 (1983).

Ross, K. F. A., and Billing, E. J., "The Water and Solid Content of Living Bacterial Spores and Vegetative Cells as Indicated by Refractive Index Measurements," *Gen. Microbiol.* 16, 418 (1957).

Rousseau, D. L., Ed., *Optical Techniques in Biological Research*, Academic, New York (1984).

Tarantola, A., *Inverse Problem Theory*, Elsevier, Amsterdam (1987).

Thormlen, I., Straub, J., and Grigull, U., *J. Phys. Chem. Ref. Data* 14(4), 933 (1985).

Towmey, S., *Introduction to the Mathematics of Inversion in Remote Sensing and Indirect Measurements*, Elsevier, New York (1979).

van de Hulst, H. C., *Light Scattering by Small Particles*, Wiley, New York (1957).

Wolf, E., and Born, M., *Principles of Optics*, Macmillan, New York (1964).

Zollars, R. L., *J. Coll. Interface Sci.* 74, 163 (1980).

It may be appreciated by one skilled in the art that additional embodiments may be contemplated, including systems and methods for characterizing other bodily fluids and their constituents, such as, but not limited to, saliva and spinal fluid. In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for determining the viability of platelets contained in a fluid sample comprising the steps of:
   providing an at least partially translucent sample bag comprising a pH-indicator inside the sample bag;
   placing the fluid sample into the at least partially translucent sample bag in contact with the pH indicator;
   measuring the pH of the sample using the pH-indicator; and determining the viability of the platelets contained in the fluid sample using the measured pH.

2. The method according to claim 1, wherein the pH-indicator comprises a pH-sensitive chemical substance.

3. The method recited in claim 2, wherein the chemical substance is selected from a group consisting of phenol red and cresol purple.

4. The method recited in claim 1, wherein the measuring step comprises performing a photometric spectral measurement over a predetermined wavelength range.

5. The method recited in claim 4, wherein the range comprises 400 to 700 nm.

6. The method according to claim 1, wherein the pH-indicator undergoes a color change due to a change in the pH of the fluid sample, and the measuring step comprises making a visual determination of the color of the pH indicator.

7. A method for determining the viability of platelets contained in a fluid sample comprising the steps of:
   providing an at least partially translucent sample bag comprising a non-bleeding pH-indicator inside the sample bag;
   placing the fluid sample into the at least partially translucent sample bag in contact with the pH indicator;
   measuring the pH of the sample using the pH-indicator by performing a photometric spectral measurement over a predetermined wavelength range; and
   determining the viability of the platelets contained in the fluid sample using the measured pH.

8. The method recited in claim 7, wherein the range comprises 400 to 700 nm.

* * * * *